(12) United States Patent
Mostafavi (10) Patent No.: US 7,756,244 B2
(45) Date of Patent: Jul. 13, 2010

(54) SYSTEMS AND METHODS FOR DETERMINING OBJECT POSITION

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 245 days.

(21) Appl. No.: 11/473,490

(22) Filed: Jun. 22, 2006

(65) Prior Publication Data

US 2007/0297575 A1 Dec. 27, 2007

(51) Int. Cl.
*A61B 6/08* (2006.01)
(52) U.S. Cl. ........................................ 378/20; 378/205
(58) Field of Classification Search .............. 378/4–20, 378/163, 205, 207
See application file for complete search history.

(56) References Cited

U.S. PATENT DOCUMENTS

| | | | |
|---|---|---|---|
| 4,283,828 A * | 8/1981 | Cole, Sr. ........................ | 29/256 |
| 6,148,058 A * | 11/2000 | Dobbs ........................... | 378/19 |
| 6,224,257 B1 * | 5/2001 | Launay et al. ................. | 378/207 |
| 6,364,529 B1 * | 4/2002 | Dawson ........................ | 378/207 |
| 6,923,817 B2 * | 8/2005 | Carson et al. ................. | 606/130 |
| 2002/0156484 A1 * | 10/2002 | McKernan et al. ............. | 606/98 |
| 2002/0188194 A1 * | 12/2002 | Cosman ........................ | 600/426 |
| 2004/0015176 A1 * | 1/2004 | Cosman ........................ | 606/131 |
| 2004/0068187 A1 * | 4/2004 | Krause et al. ................. | 600/443 |
| 2005/0008126 A1 * | 1/2005 | Juh et al. ...................... | 378/207 |
| 2005/0201509 A1 * | 9/2005 | Mostafavi et al. ............. | 378/8 |

OTHER PUBLICATIONS

International Search Report for corresponding application PCT/US2007/14586, 4 pages, dated Sep. 22, 2008.

* cited by examiner

*Primary Examiner*—Hoon Song
(74) *Attorney, Agent, or Firm*—Vista IP Law Group, LLP.

(57) ABSTRACT

A system for determining a position of an object includes a block having a base, and a plurality of elongate members secured to the block. A system for determining a position of an object includes a processor configured to obtain an image of portions of respective elongated members, and determine a position of an object that is coupled to the plurality of elongated members. A method of determining a position of an object includes obtaining a first image of portions of respective elongated members, and determining a first position of an object using the first image.

41 Claims, 9 Drawing Sheets

FIG. 9

SYSTEMS AND METHODS FOR DETERMINING OBJECT POSITION

FIELD

This application relates generally to systems and methods for determining object position, and more specifically, to systems and methods for determining object position using imaging technique.

BACKGROUND

Computed tomography is an imaging procedure that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. By considering one or more sections in the volume, a skilled diagnostician can often diagnose various bodily ailments such as tumors, blood clots, etc.

Computed tomography has found its principal application to examination of bodily structures or the like which are in a relatively stationary condition. However, currently available computed tomographic apparatus may not be able to generate tomographic images with sufficient quality or accuracy due to physiological movement of a patient. For example, beating of a human heart and breathing have been known to cause degradation of quality in CT images. U.S. Pat. No. 3,952,201 issued to Hounsfield, describes a system that compensates for a blurring of a radiograph due to heart motions by collecting image data of a patient at different angles while monitoring the patient's heart. The image data and the heart motion data are then correlated in a computer, and image data that was obtained when the heart's motion exceeded a threshold level is rejected.

Degradation of quality of CT images due to patient's breathing is more difficult to address than that associated with heart motion. Patients' breathing poses a unique problem to CT imaging that is different from heart motion. This is because the pattern and the period of a patient's breathing cycle is generally less consistent when compared to those of the patient's cardiac cycle. As such, while a particular phase of a cardiac cycle may be determined with sufficient accuracy, a particular phase of a breathing cycle may not be as easily determined.

Existing CT imaging systems may use a camera to determine patient position. In such CT imaging system, a marker block having a plurality of reflective elements is placed on a patient's chest. The camera is then used to sense the reflective elements on the marker block. By determining the positions of the reflective elements, a position and/or orientation of the marker block can be determined. The positional data is then considered in the construction of CT images so that patient's movement is addressed. However, adding a camera to an existing CT imaging system would add cost to the system. Also, in some cases, it may be difficult or impossible to install a camera in an operation room due to various mechanical and electrical constraints.

SUMMARY

In accordance with some embodiments, a system for determining a position of an object includes a block having a base, and a plurality of elongate members secured to the block.

In accordance with other embodiments, a system for determining a position of an object includes a processor configured to obtain an image of portions of respective elongated members, and determine a position of an object that is coupled to the plurality of elongated members.

In accordance with other embodiments, a method of determining a position of an object includes obtaining a first image of portions of respective elongated members, and determining a first position of an object using the first image.

Other aspects and features will be evident from reading the following detailed description of the embodiments.

BRIEF DESCRIPTION OF THE DRAWINGS

The drawings illustrate the design and utility of embodiments, in which similar elements are referred to by common reference numerals. In order to better appreciate how advantages and objects of the embodiments are obtained, a more particular description of the embodiments will be illustrated in the accompanying drawings.

DETAILED DESCRIPTION OF THE EMBODIMENTS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of embodiments. They are not intended as an exhaustive description of the invention or as a limitation on the scope of the invention. In addition, an aspect described in conjunction with a particular embodiment is not necessarily limited to that embodiment and can be practiced in any other embodiments.

Figure 1:
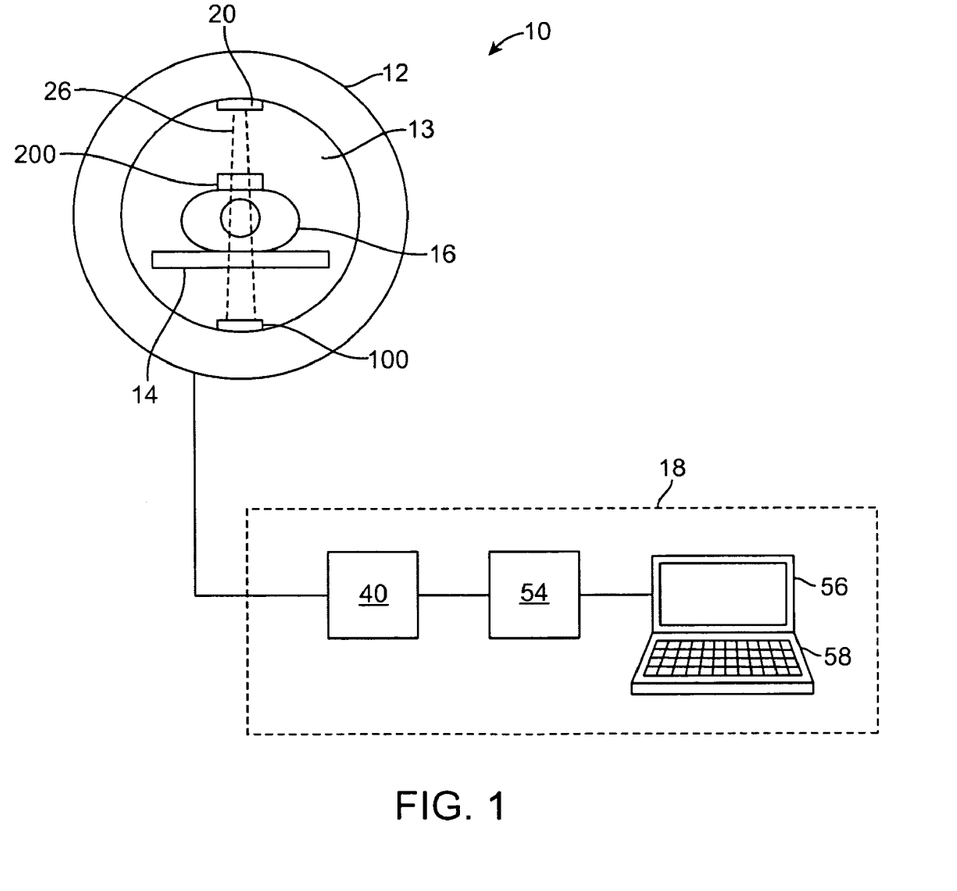
FIG. 1 illustrates a system for determining object position in accordance with some embodiments.

FIG. 1 illustrates a radiation system 10 in accordance with some embodiments. The system 10 includes a gantry 12 having an opening (or bore) 13, a patient support 14 for supporting a patient 16, and a control system 18 for controlling an operation of the gantry 12. The system 10 also includes a radiation source 20 that projects a beam 26 of radiation towards the patient 16 while the patient 16 is positioned at least partially within the opening 13. The radiation source 20 can be configured to generate a cone beam, a fan beam, or other types of radiation beams in different embodiments. The system 10 further includes an imager 100 located opposite from the radiation source 20.

In the illustrated embodiments, the radiation source 20 is a diagnostic radiation source for providing diagnostic energy (e.g., energy that is suitable for generating an image). In other embodiments, in addition to being a diagnostic radiation source, the radiation source 20 can also be a treatment radiation source for providing treatment energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In some embodiments, if the radiation source 20 is capable of delivering treatment energy, the system 10 can further include a collimator system (not shown) secured to the radiation source 20 for controlling a delivery of the radiation beam 26. In further embodiments, the radiation source 20 is a treatment radiation source configured to deliver radiation having an energy level suitable for treatment.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during an imaging procedure, the gantry 12 rotates about the patient 16. The operation of the radiation source 20 and the gantry 12, are controlled by the control 40, which provides power and timing signals to the radiation source 20, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54. In some embodiments, if the system 10 includes a collimator system, the operation of the collimator system is also controlled by the processor 54. In further embodiments, the control 40 also controls a position of the patient support 14. For example, the control 40 may cause the patient support 14 to translate relative to the opening 13.

In the illustrated embodiments, the imager 100 is located next to the opening 13 and opposite from the radiation source 20. In some embodiments, the imager 100 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 100 can have a curvilinear surface (e.g., a partial circular arc). Such configuration is beneficial in that each of the imaging elements of the imager 100 is located substantially the same distance from the radiation source 20. In an alternative embodiment, the imager 100 may have a rectilinear surface or a surface having other profiles. The imager 100 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 100 may use different detection schemes. For example, in alternative embodiments, instead of having the conversion layer, the imager 100 may include a photoconductor, which generates electron-hole-pairs or charges in response to radiation.

During a diagnostic procedure, the radiation source 20 generates and directs a radiation beam 26 towards the patient 16, while the detector 100 measures the radiation absorption at a plurality of transmission paths defined by the radiation beam during the process. The detector 100 produces a voltage proportional to the intensity of incident radiation, and the voltage is read and digitized for subsequent processing in a computer, such as the processor 54 or another processor. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning, and/or to verify a position of a target tissue.

It should be noted that the radiation system 10 should not be limited to the configuration described previously, and that the radiation system 10 can also have other configurations in other embodiments. For example, in other embodiments, instead of a ring-configuration, the radiation system 10 can have a C-arm configuration. Also, in other embodiments, the radiation system 10 can include an arm to which the radiation source 20 is secured. In further embodiments, the radiation system 10 can have configurations that are known in the art of radiation systems.

As shown in FIG. 1, the radiation system 10 also includes a marker block device 200 that is coupled to the patient 16. The device 200 is used during an operation of the system 10 to determine a position of at least a portion of the patient 16. A method of using the device 200 in accordance with various embodiments will be discussed below.

Figure 2A:
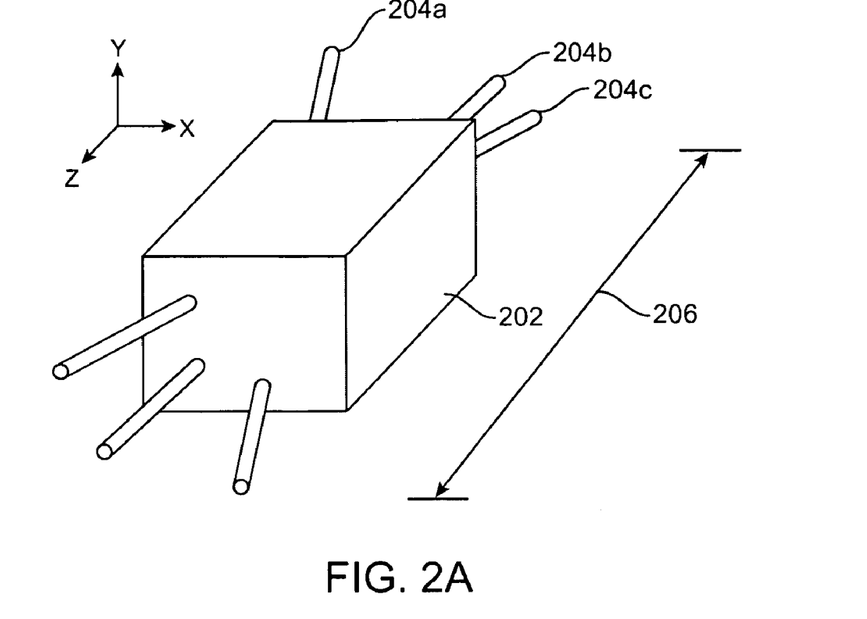
FIG. 2A illustrates a device for use to determine a position of an object in accordance with some embodiments.

FIG. 2A illustrates the device 200 for use with the radiation system 10 of FIG. 1 in accordance with some embodiments. The device 200 includes a block 202 and a plurality of rods 204a-204c. In the illustrated embodiments, the device 200 includes three rods 204. In other embodiments, the device 200 includes more than three rods 204. The block 202 is not limited to the rectangular shape shown in the figure, and can have other shapes in other embodiments. For example, in other embodiments, the block 202 has a cylindrical shape or a hemispherical shape. In the illustrated embodiments, the device 200 has a length 206 that is at least equal to a length of a body structure desired to be imaged by the system 10 (e.g., for diagnostic, treatment planning, and/or treatment purposes). For example, in some embodiments, the rods 204 have respective lengths such that the length 206 of the device 200 is a value that is between 5 inches and 15 inches, and more preferably, approximately 10 inches (e.g., 10 inches+1 inch). In other embodiments, the length 206 may be other values. In further embodiments, the length 206 of the device 200 may be determined to account for respiration motion. For example, if an object desired to be imaged has a length of 5 inches, and respiration motion will cause the object to shift 0.5 inch in each direction, then the length 206 of the device 200 will be at least 5+0.5+0.5=6 inches.

Figure 2B:
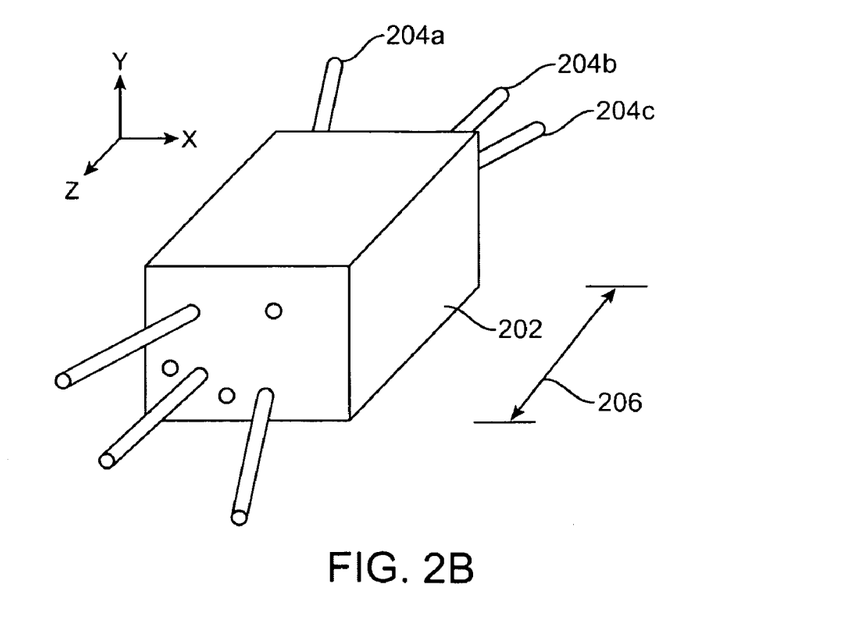
FIG. 2B illustrates a device for use to determine a position of an object in accordance with other embodiments.

In further embodiments, the rods 204 are detachably coupled to the block 202. In such cases, the block 202 can include a plurality of slots, with the number of slots being greater than the number of rods 204 (FIG. 2B). During use, a user can selectively choose a subset of slots to which the rods 204 are inserted. Such feature allows the user to create different arrangements of rods 204.

Figure 3:
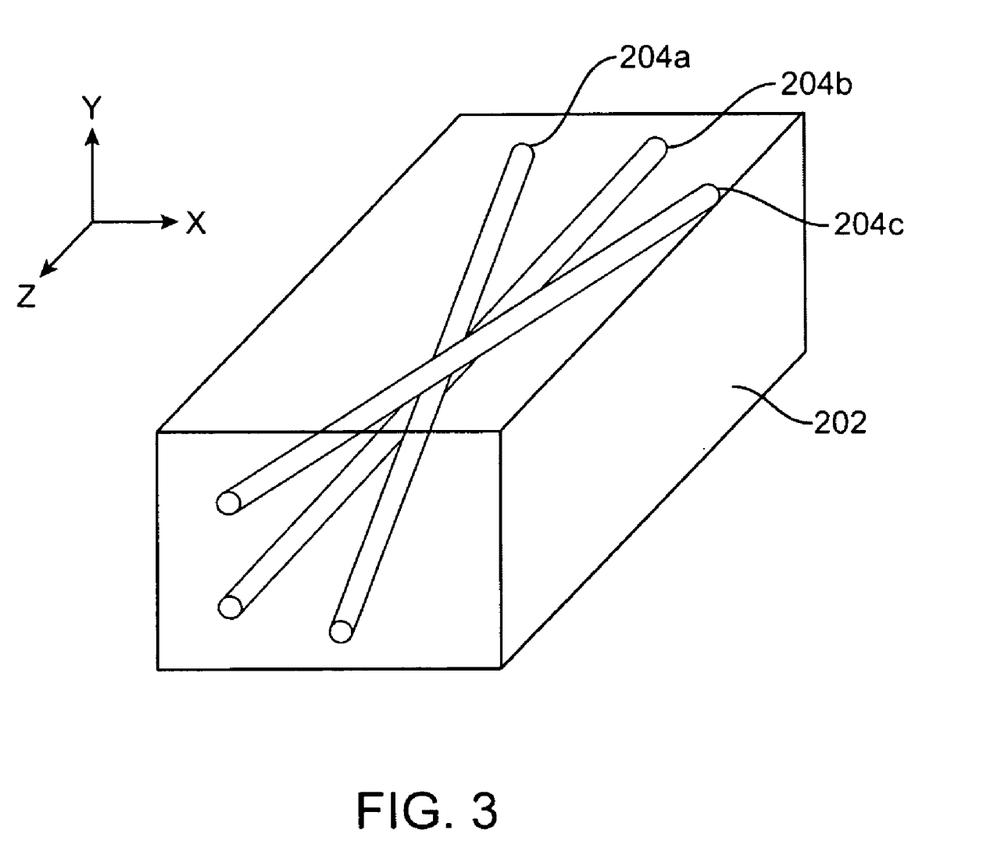
FIG. 3 illustrates a device for use to determine a position of an object in accordance with other embodiments.

FIG. 3 illustrates the device 200 for use with the radiation system 10 of FIG. 1 in accordance with other embodiments. The device 200 is similar to that shown in FIG. 2A, and includes a block 202 and a plurality of rods 204a-204c. However, in the illustrated embodiments, the block 202 is made sufficiently large to encapsulate the rods 204a-204c. In the illustrated embodiments, the device 200 includes three rods 204. In other embodiments, the device 200 includes more than three rods 204. The block 202 is not limited to the rectangular shape shown in the figure, and can have other shapes in other embodiments. For example, in other embodiments, the block 202 has a cylindrical shape or a hemispherical shape. In some embodiments, the block 202 may be made from a material having a clear color, thereby allowing a user to see the rods 204 embedded therein.

In the above embodiments, the rods 204 of the device 200 have circular cross section. However, in other embodiments, the rods 204 may have different cross sectional shapes. For examples, in other embodiments, each of the rods 204 may have a rectangular shape, a triangular shape, an elliptical shape, a diamond shape, an octagon shape, or an irregular shape. In further embodiments, one or more of the rods 204 may have a different cross sectional shape and/or size that is different from another one(s) of the rods 204. Such feature is advantageous in that it allows an image of a portion of a rod 204 to be identified and distinguished from an image of a portion of another rod 204.

Figure 4:
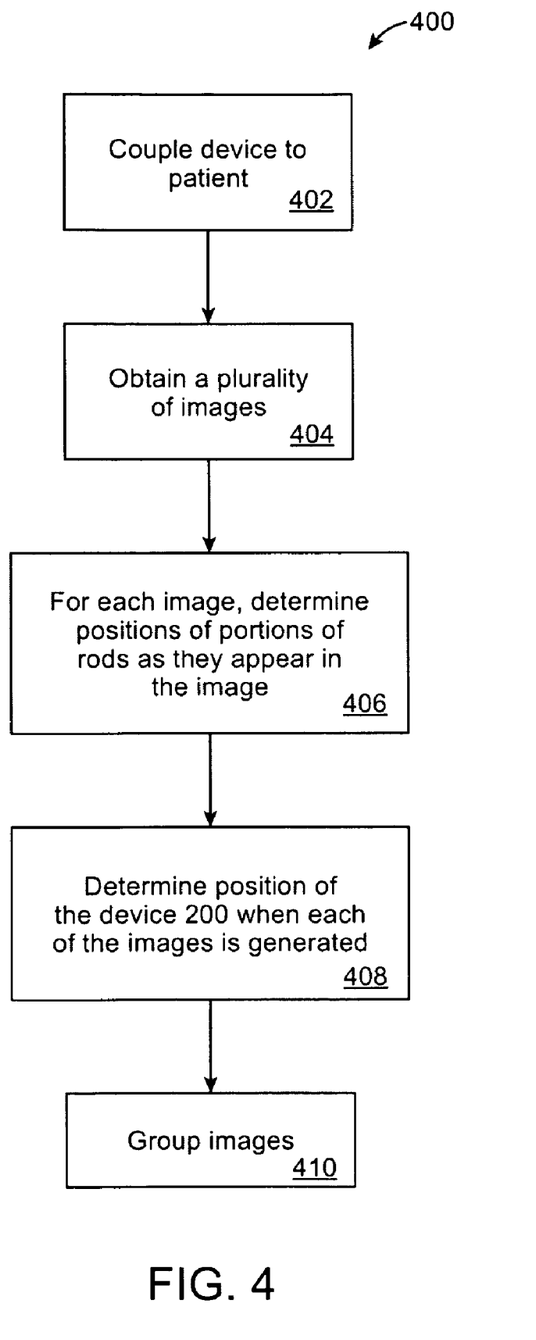
FIG. 4 illustrates a method of using the system of FIG. 1 in accordance with some embodiments.

A method 400 of using the radiation system 10 in accordance with some embodiments will now be described with reference to FIG. 4. First, the marker block device 200 is coupled to the patient 16, with the patient 16 being placed on the patient support 14 (Step 402). In the illustrated embodiments, the device 200 is placed on the patient's chest, and is coupled to the patient 16 by friction. Alternatively, the device 200 can be coupled to the patient at other positions, and may be further secured to the patient 16 via an adhesive (e.g., a tape) or a strap.

In the illustrated embodiments, the device 200 is positioned above a patient's chest, with the length 206 of the device 200 covering a length of a body structure (e.g., internal tissue) desired to be imaged. Also, in the illustrated embodiments, the device 200 is oriented such that its Z-axis is approximately parallel to (e g., ±15° from) an axis of the gantry 12. In other embodiments, the device 200 can be oriented at other angles relative to the axis of the gantry 12. In other embodiments, the device 200 may be positioned on other parts of the patient, e.g., on the abdomen, or on the back of the patient when the patient is in a prone position.

Next, an image acquisition procedure is performed to obtain a plurality of images of a portion (e.g., a target region) of the patient 16 (Step 404). For example, a computed tomography (CT) procedure may be performed using the radiation source 20 and the detector 100 to create a plurality of images at different times. In some embodiments, each created image is an image slice generated from a full, or a 180°-plus-fan angle, rotation of the gantry 12. In some cases, if a multi-slice scanner is used, each image slice then corresponds to a single row on the multi-slice scanner. Because the time of acquisition of such image slice is relatively small, the created image slice may be considered as generated at a point in time. CT procedure is known in the art of imaging, and will not be described in detail. In other embodiments, the plurality of images may be obtained using different imaging techniques and imaging systems. For example, in other embodiments, the system 10 may be a PET imaging system, in which cases, a PET imaging technique is performed to obtain a plurality of PET image slices.

Figure 5:
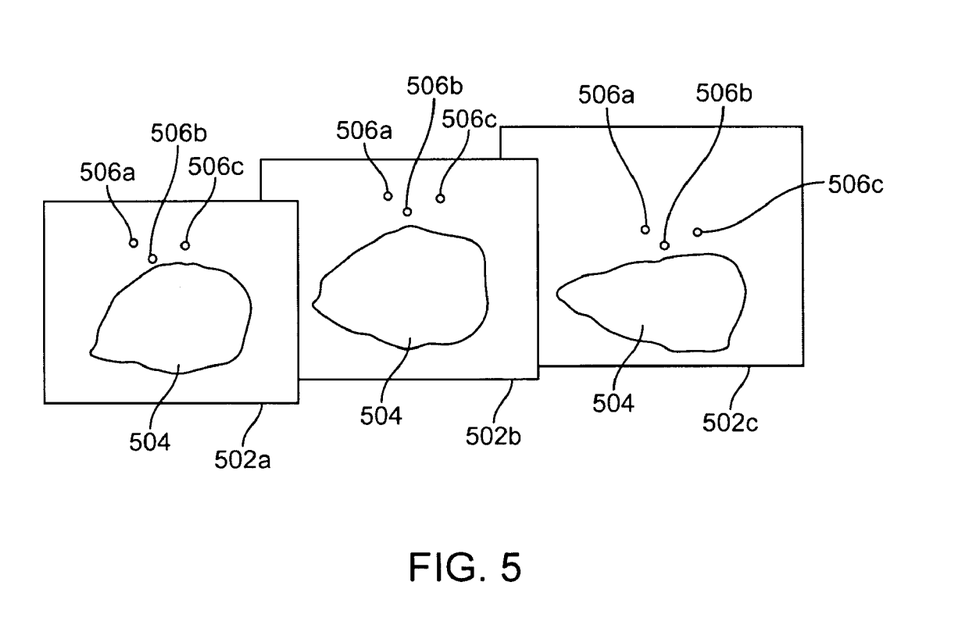
FIG. 5 illustrates a plurality of images generated using the system of FIG. 1.

Because the rods 204 of the device 200 extend the length of the target tissue that is being imaged, each of the images generated using the system 10 will include images (contrast features) of portions of respective rods 204. FIG. 5 illustrates an example of three images 502a-502c of a body structure 504 generated from step 404. The images 502a-502c are image slices (which, for examples, may be CT/X-ray slices, PET slices, etc.) generated at different times.

Returning to FIG. 4, for each of the generated images, the positions of the rods 204 as they appear in each image are determined (Step 406). This can be accomplished using various techniques. In some embodiments, the positions of the rods 204 can be determined manually. In other embodiments, the processor 54 is configured (e.g., programmed, constructed, etc.) to determine the positions of the rods 204. In such cases, the processor 54 is configured to analyze each image by performing an image recognition procedure against each image. For example, the image recognition procedure can be one that is designed to sense an object in an image based on a shape, an intensity, or other attributes, of the object as it appears in the image. Image recognition techniques are well known in the art of imaging, and therefore, would not be described in detail.

Figure 7:
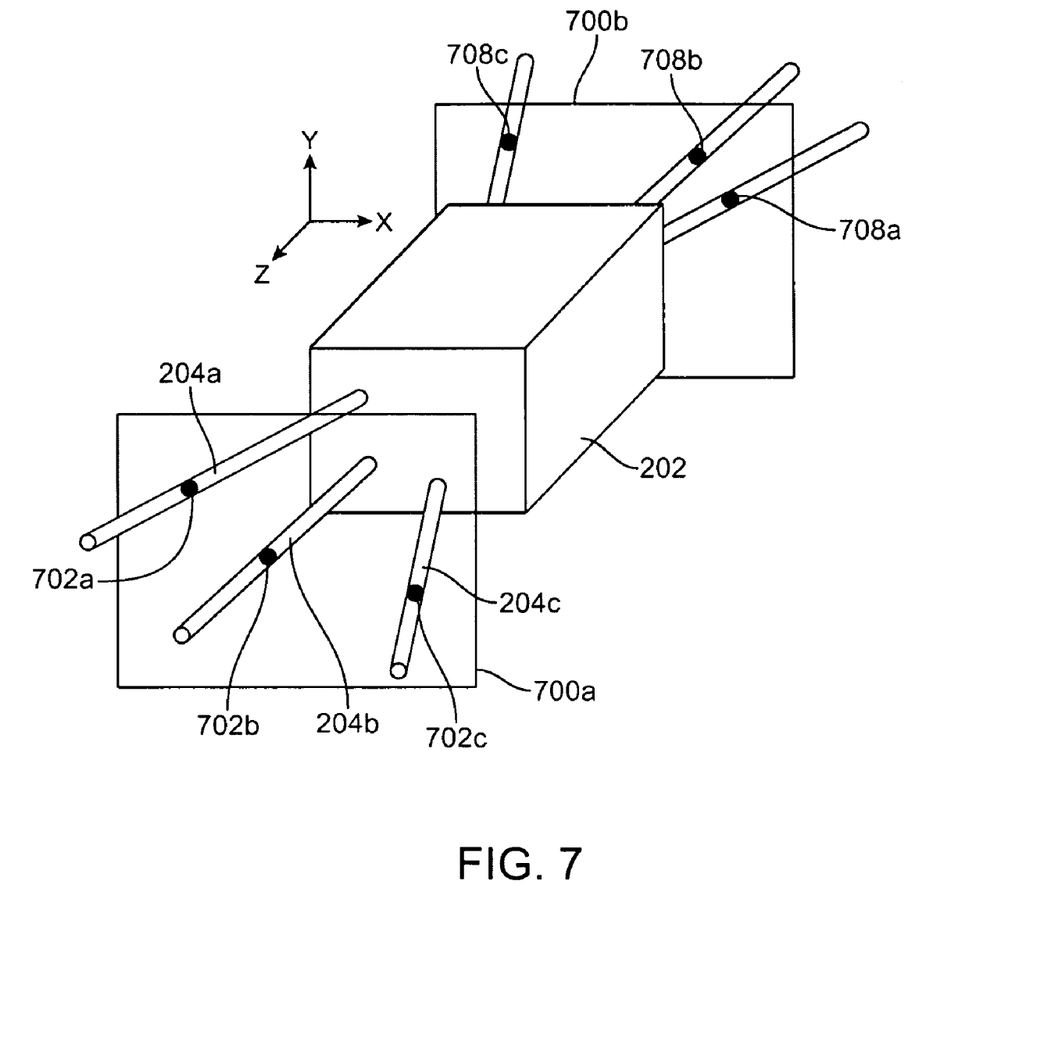
FIG. 7 illustrates an example of two images each of which having contrast features of elongated objects.

Next, for each image, the position and/or orientation of the block 200 relative to a reference coordinate system when the image is obtained is determined (Step 408). The reference coordinate system can be a coordinate of the system 10, a coordinate system associated with the patient support 14, or a user prescribed coordinate system. In the illustrated embodiments, the position and/or orientation of the block 200 when each image is obtained is determined based on a pattern of the rods 204 as they appear in each image. FIG. 7 shows an example of an image 700a obtained using the system 10. The image 700a has images (contrast features) 702a-702c of portions of the respective rods 204a-204c. In some embodiments, the positions of the images 702a-702c, the relative positions of the rods 204a-204c, and the relative positions between the block 202 and the rods 204, can be used to calculate the position and orientation of the block 202. The position and orientation of the rods 204 relative to each other are configured such that a unique spatial pattern of the contrast features will result from each block position and orientation. For example, in some embodiments, no parallel or coplanar pairs of the rods 204 are allowed.

Figure 8:
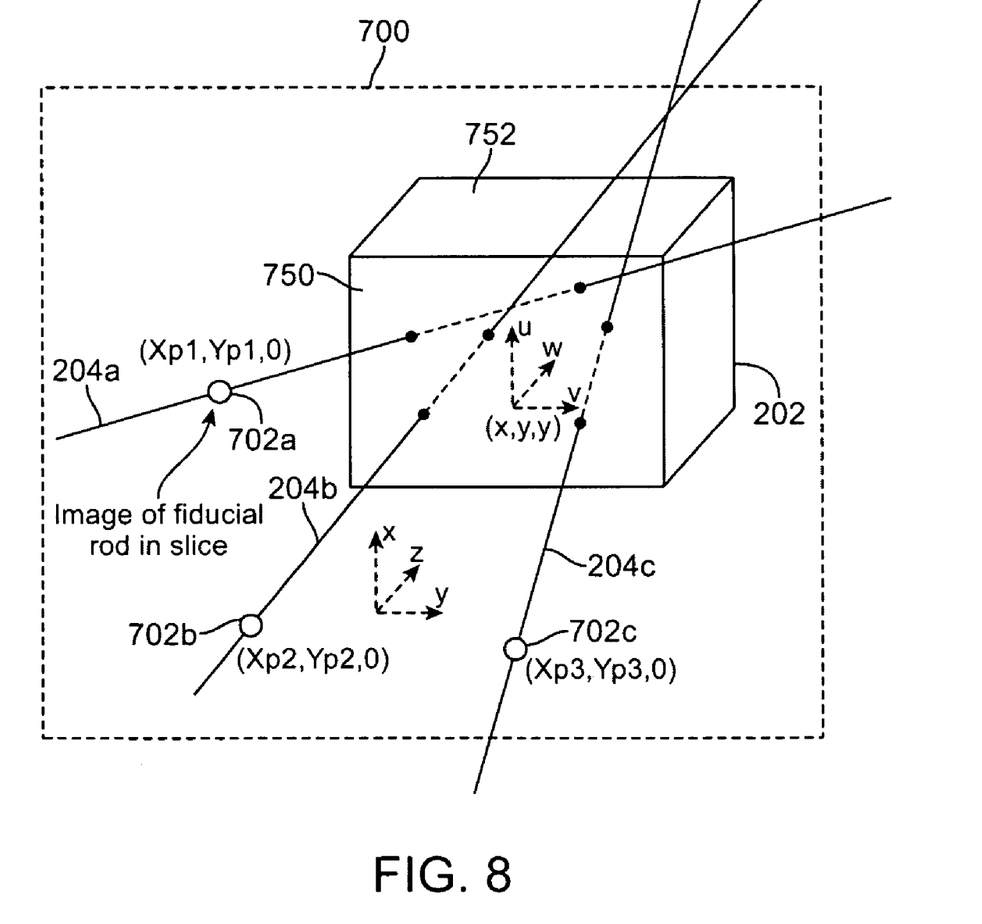
FIG. 8 illustrates an example of a geometry of a block with rods relative to an image slice plane.

FIG. 8 illustrates an example of a geometry of the block 202 with rods 204a-204b relative to an image slice plane 700. The slice is assumed to be the Z=0 plane of measurement coordinates X, Y, Z. The coordinates of the intersection of the rods 204 with this plane 700 are used to determine the position (Xb, Yb, Zb) of the block 202 and its orientation (e.g., rotation of its local coordinate axes (u, v, w) relative to the coordinate system (X, Y, Z)). The local survey coordinates (u, v, w) of the block 202 is assumed to be at the block 202 center and aligned with the block 202 edges as shown in the figure. The 3D coordinates of the point of intersection of each rod 204 with the front face 750 of the block 202 is denoted by (uf, vf, wf). Similarly the 3D coordinates of the point of intersection of each rod 204 with the rear face 752 of the block 202 is denoted by (ur, vr, wr).

In the illustrated example, the condition that no two of the rods 204 are coplanar is imposed. Also, because of symmetry, w=wr=−wf. The objective is to estimate the position and rotation angles (six degrees of freedom (dof)) of the block 202 relative to the slice reference coordinates. Let (X, Y, Z) be the position coordinates and ($\alpha,\beta,\gamma$) be the rotation angles of the block relative to the Z, X, and Y coordinates respectively. Then the image coordinates of a rod 204, i.e., its intersection 702 with the slice plane 700 is given by:

$$Xp = -((1+a^*x+b^*z)/(a^*\cos(\beta)^*\cos(\alpha)-b^*\sin(\beta))) +$$
$$(((1+c^*y+d^*z)^*(a^*\cos(\beta)^*\cos(\alpha)-b^*\sin(\beta)) -$$
$$(1+a^*x+b^*z)^*(-(d^*\sin(\beta))+c^*\cos(\beta)^*\sin(\alpha)))^*$$
$$(-(a^*\cos(\gamma)^*\sin(\alpha))+b^*\cos(\beta)^*\sin(\gamma)+a^*\cos$$
$$(\alpha)^*\sin(\beta)^*\sin(\gamma))/((a^*\cos(\beta)^*\cos(\alpha)-b^*\sin$$
$$(\beta))^*(-((-(d^*\sin(\beta))+c^*\cos(\beta)^*\sin(\alpha))^*(-$$
$$(a^*\cos(\gamma)^*\sin(\alpha))+b^*\cos(\beta)^*\sin(\gamma)+a^*\cos(\alpha)$$
$$^*\sin(\beta)^*\sin(\gamma)))+(a^*\cos(\beta)^*\cos(\alpha)-b^*\sin(\beta))^*$$
$$(c^*\cos(\alpha)^*\cos(\gamma)+d^*\cos(\beta)^*\sin(\gamma)+c^*\sin(\beta)$$
$$^*\sin(\alpha)^*\sin(\gamma))))$$

$$Yp = -(((1+c^*y+d^*z)^*(a^*\cos(\beta)^*\cos(\alpha)-b^*\sin(\beta)) -$$
$$(1+a^*x+b^*z)^*(-(d^*\sin(\beta))+c^*\cos(\beta)^*\sin(\alpha)))/$$
$$(-((-(d^*\sin(\beta))+c^*\cos(\beta)^*\sin(\alpha))^*(-(a^*\cos(\gamma)$$
$$^*\sin(\alpha))+b^*\cos(\beta)^*\sin(\gamma)+a^*\cos(\alpha)^*\sin(\beta)$$
$$^*\sin(\gamma)))+(a^*\cos(\beta)^*\cos(\alpha)-b^*\sin(\beta))^*(c^*\cos$$
$$(\alpha)^*\cos(\gamma)+d^*\cos(\beta)^*\sin(\gamma)+c^*\sin(\beta)^*\sin(\alpha)$$
$$^*\sin(\gamma))))$$

where the constants a, b, c, and d are determined by the position of a rod 204 relative to the block 202. In particular, these constants are determined by the coordinates of intersection points 702 of the rod 204 with the front and rear faces 750, 752 of the block 202 as follows.

$$a = -2/(vr+vf)$$

$$b = (1/w)^*(vr-vf)/(vr+vf)$$

$$c = -2/(ur+uf)$$

$$d = (1/w)^*(ur-uf)/(ur+uf)$$

As illustrated in the example, each rod 204 produces a pair of equations for Xp and Yp as a function of the block 202 six dof as defined above. For N rods, N>=3, there will be six or more equations of six unknowns, namely the 3D position and three rotations of the block 202. In some embodiments, these equations can be solved using the iterative Gauss technique. The constraint of no two rods 204 being coplanar may be used in obtaining a solution. Another constraint that may be used in obtaining a solution is that three or more rods 204 be in the field of view of the image slice 700, i.e. intersect with the slice plane 700. It should be noted that the algorithm that may be used to determine the block 202 position and orientation is not limited to the example described, and that other algorithms may also be used in other embodiments.

Returning to FIG. 4, as a result of step 408, a trajectory representing positions and/or orientations of the block 202 over time may be determined based on the rods positions in the image slices, with each image slice corresponding to a point on the trajectory. For example, positions of the block 202 determined from step 408 may be plotted in a graph, with its y-axis representing values of the block 202 positions, and x-axis representing values of time. In such cases, an image slice (generated at a time) that is used to determine a block position is associated with a point in the graph, wherein the x value of the point represents the time at which the image slice is generated (or considered to be generated), and the y value of the point represents the determined position of the block 202. In other embodiments, orientations of the block 202 determined from step 408 may be plotted in a graph, with its y-axis representing values of the block 202 orientations, and x-axis representing values of time.

As shown in the illustrated embodiments, through the use of the rods 204, the position and/or orientation of the block 200 when the image 700a is obtained can be determined, even when the plane of the image is located away from the block 202. In some embodiments, the plurality of images at step 404 are obtained when a patient is undergoing a breathing cycle (or a portion of a breathing cycle). In such cases, the position and/or orientation of the block 202 when each image is obtained during the cycle will be determined using the above algorithm.

Next, the plurality of images generated at step 404 are grouped or binned into one or more sets (Step 410). In some embodiments, the grouping of the images can be performed based on the determined positions of the device 200 associated with the respective images. In such cases, a plurality of prescribed amplitude slots, each of which is a range of amplitudes, can be used to group the images. For example, if two position data points of the device 200 have amplitude values of 1 inch and 1.5 inch, respectively, and a prescribed amplitude slot has a range of 0.8 inch to 2 inches, then images associated with both of the position data points would be binned into the amplitude slot.

In other embodiments, the grouping of the images can be performed based on phases of a physiological cycle undergone by the patient when the respective images are obtained. As used in this specification, the term "phase" refers to a degree of completeness of a physiological cycle (e.g., a breathing cycle or a cardiac cycle) of a portion of a patient. For example, the phase may have a value that is between 0% and 100%. In such cases, a phase value of 50% represents a half-completion of a physiological cycle. As another example, the phase may have a value that is between 0° and 360°. In such cases, a phase value of 18° represents a half-completion of a physiological cycle.

Figure 6:
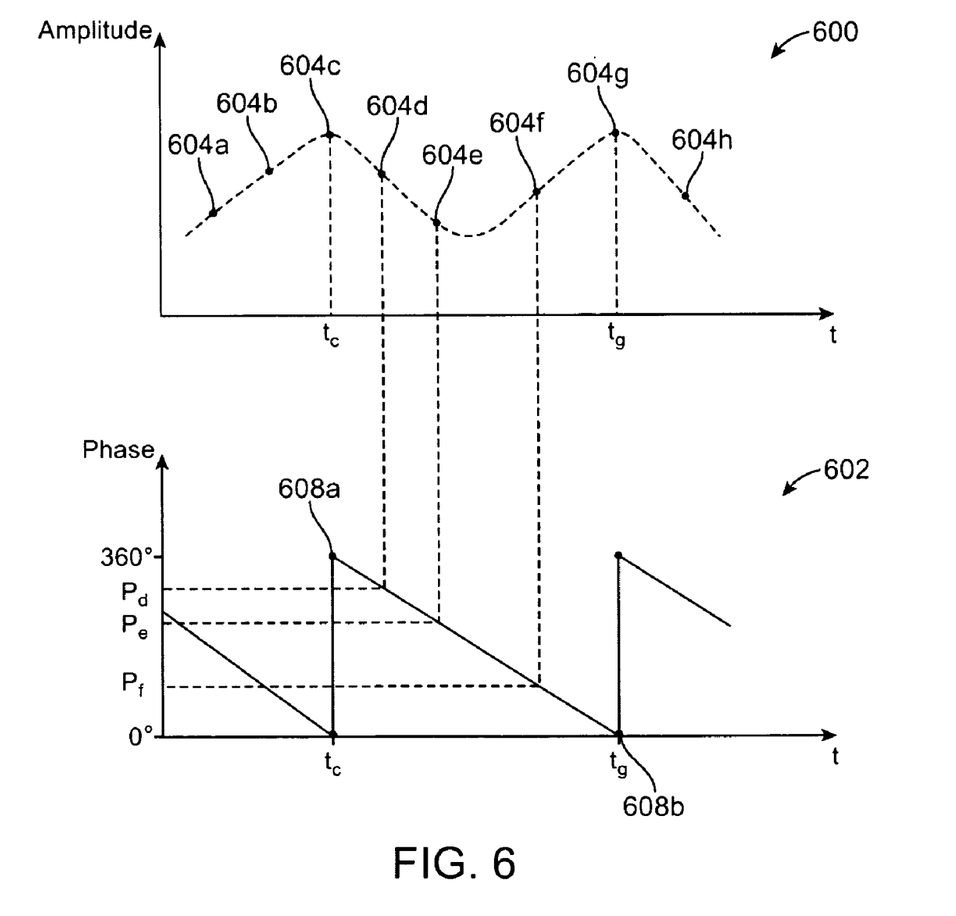
FIG. 6 illustrates an example of an amplitude diagram aligned with a phase diagram.

The phase of a physiological cycle when an image is obtained can be determined from the position data of the device 200 determined in step 408. FIG. 6 illustrates an example of a technique for determining a phase of a physiological cycle. As shown in the figure, an amplitude diagram 600 illustrates how a position of the device 200 (and therefore, an amplitude of a motion undergone by a portion of the patient 16) varies with time. Such amplitude diagram 600 may be created by considering a plurality of position data for the device 200. Each point 604 in the amplitude diagram 600 represents a position of the device 200 when an image is generated at a corresponding time t. As shown in the example, data points 604c and 604g represent two adjacent peak values at time $t_c$ and $t_g$, respectively. In some embodiments, the phase diagram 602 can be constructed by determining a line 606 that connects two points 608a, 608b, with the first point 608a being ($t_c$, 360), and the second point being ($t_g$, 0). In other embodiments, the phase diagram 602 can be constructed by determining a line 606 that connects two points 608a, 608b, with the first point 608a being ($t_c$, 0), and the second point being ($t_g$, 360). As shown in the figure, the phase diagram 602 shows how a degree of completion of a physiological cycle varies over time. In the example, a phase value of 360° or 0° corresponds to a peak of a physiological cycle.

After the line 606 has been determined, the phase for each of the data points 604d-604f that is between the points 604c and 604g can be determined by projecting a vertical line from each point, and determining the phase value that corresponds to the intersection between the vertical line and the line 606. In other embodiments, the phase value for each image can be determined mathematically (e.g., performed by processor 54). For example, the phase for data point 604d can be determined by the equation, $P_d=360*(t_g-t_d)/(t_g-t_c)$. It should be noted that the method of determining the phase associated with each image should not be limited to the examples described previously, and that other similar techniques can also be used to determine the phase for each image.

In some embodiments, the grouping of the images can be performed based on the determined phase values. In such cases, a plurality of prescribed phase slots, each of which is a range of phase values, can be used to group the images. For example, if data point 604d and data point 604e have associated phase values of 350° and 344°, respectively, and a prescribed phase slot has a range of 340° to 355°, then images associated with respective data points 604d, 604e would be binned into the phase slot.

In some embodiments, after the images have been grouped into one or more sets (e.g., based on amplitude or phase), each set of images is then used to construct a three-dimensional CT image. In some cases, if a plurality of three-dimensional CT images are generated for different phases of a physiological cycle, the CT images can be displayed in a sequence to form a video. Alternatively, the grouping of the images in step 410 is not needed, and the determined positions of the block position and/or orientation in step 408 may be used in other procedure(s), e.g., diagnostic procedure, treatment planning, and treatment procedure.

As shown in the above embodiments, using the device 200 to determine a position of the patient 12 is advantageous in that it obviates the need to use a separate optical device for sensing a marker block. The method 400 of using the system 10 is not limited to the example discussed previously. In other embodiments, one or more steps can be combined with another step in the method 400. In further embodiments, the method 400 needs not include all of the steps 402-410.

In other embodiments, the above procedure can be performed for other images that are obtained at a different position along an axis of the gantry 12. For example, as shown in FIG. 7, another image 700b spaced away from the first image 700a can be obtained using the system 10. The image 700b has images (contrast features) 708a-708c of portions of the respective rods 204a-204c. Due to the orientation of the rods 204, the pattern of the images 708a-708c in the image 700b is different from the pattern of the images 702a-702c in the image 700a. In some embodiments, a plurality of images are obtained at such image plane when a patient is undergoing a breathing cycle (or a portion of a breathing cycle). In such cases, each of the images will be associated with a position of the block 202 using the above algorithm, as similarly discussed.

Although the system 10 has been described with reference to generating CT images, in other embodiments, the system 10 can be any of other types of imaging machines that are capable of generating images. For example, in other embodiments, system 10 can be a MR system for generating MR images. In further embodiments, the system 10 can be a PET system for generating PET images, or a SPECT system for generating SPECT images. In further embodiments, the system 10 can be other types of imaging systems, as long as it is capable of generating an image slice. Further, in other embodiments, the system 10 can be any of a variety of machines, such as a diagnostic machine, a simulator, a inspection machine, or another machine that may or may not be for medical use.

Computer System Architecture

Figure 9:
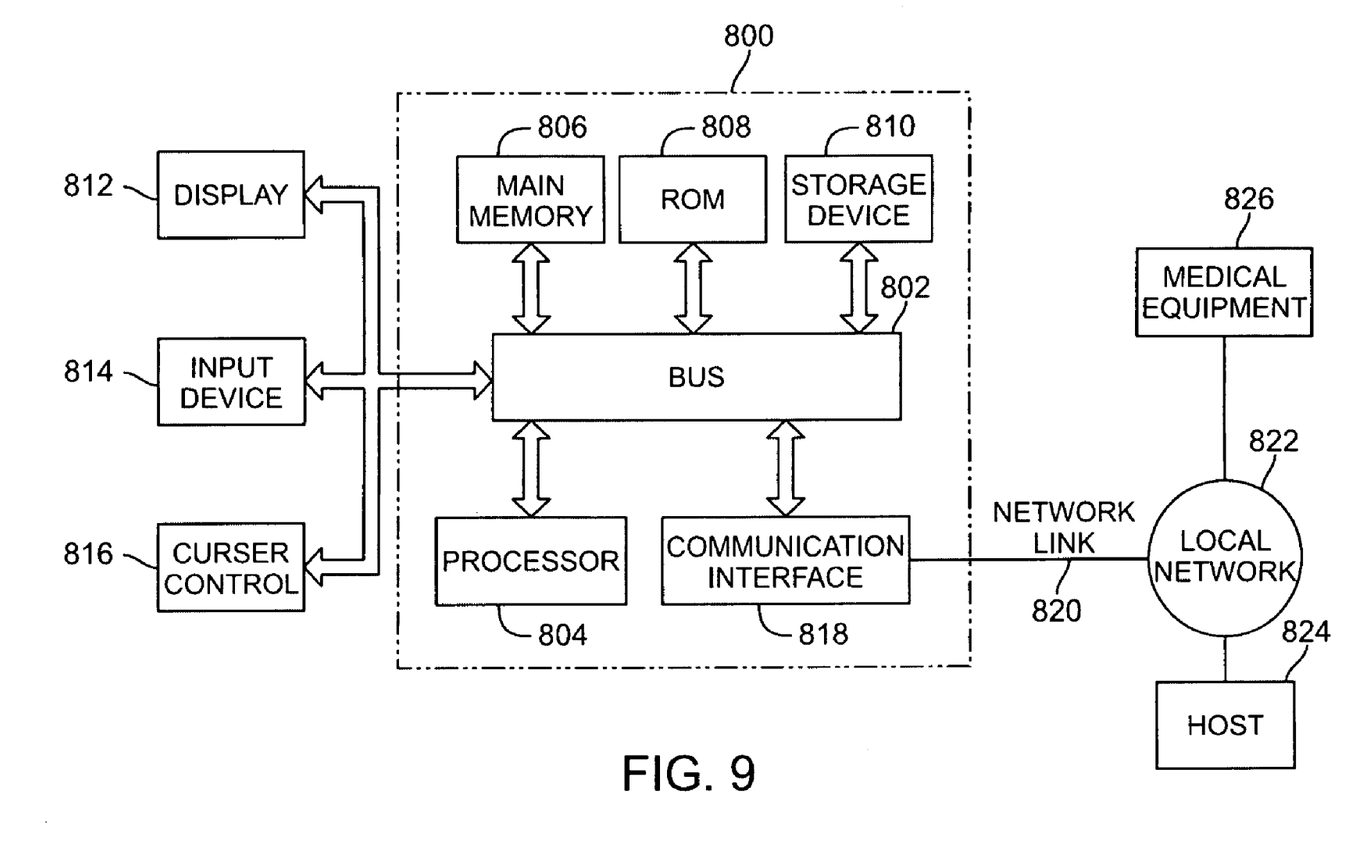
FIG. 9 illustrates a block diagram of a computer system that can be used to perform various functions described herein in accordance with some embodiments.

FIG. 9 is a block diagram illustrating an embodiment of a computer system 800 that can be used to perform various functions described herein. Computer system 800 includes a bus 802 or other communication mechanism for communicating information, and a processor 804 coupled with the bus 802 for processing information. The processor 804 may be an example of the processor 54, or alternatively, an example of a component of the processor 54, of FIG. 1. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 87, such as a cathode ray tube (CRT), for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 87. This input device typically has two degrees of freedom in two axes, a first axis (e.g., x) and a second axis (e.g., y), that allows the device to specify positions in a plane.

In some embodiments, the computer system 800 can be used to perform various functions described herein. According to some embodiments of the invention, such use is provided by computer system 800 in response to processor 804 executing one or more sequences of one or more instructions contained in the main memory 806. Those skilled in the art will know how to prepare such instructions based on the functions and methods described herein. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to equipment 826, such as any of the devices herein (e.g., device 166, system 10, patient support system 200, etc.), or a switch operatively coupled to any of the devices described herein. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network (s), the network link 820, and the communication interface 818.

Although particular embodiments have been shown and described, it will be understood that it is not intended to limit the claimed inventions, and it will be obvious to those skilled in the art that various changes and modifications may be made without departing from the spirit and scope of the application. For example, in other embodiments, the system 10 may not include one or more of the components described herein. Also, the operations performed by the processor 54 can be performed by any combination of hardware and software, and should not be limited to particular embodiments comprising a particular definition of "processor." In addition, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A system for determining a position of an object, comprising:
   a block having a base;
   a plurality of elongated markers secured to the block, wherein the plurality of elongated markers comprises a first rod and a second rod, the first rod being non-parallel relative to the second rod; and
   an imaging system for obtaining an image of respective portions of the plurality of elongated markers;
   wherein the first rod has a first end, a second end, and a length between the first and second ends, the first end is exposed outside the block, and a part of the length is located within the block; and
   wherein the imaging system has a x-ray source and an imager.

2. A system for determining a position of an object, comprising:
   a block having a base;
   a plurality of elongated markers secured to the block, wherein the plurality of elongated markers comprises a first rod and a second rod, the first rod being non-parallel relative to the second rod; and
   an imaging system for obtaining an image of respective portions of the plurality of elongated markers;
   wherein the first rod has a first end, a second end, and a length between the first and second ends, the first end is exposed outside the block, and a part of the length is located within the block; and
   wherein the imaging system comprises a computed tomography system.

3. A system for determining a position of an object, comprising:
   a block having a base;
   a plurality of elongated markers secured to the block, wherein the plurality of elongated markers comprises a first rod and a second rod, the first rod being non-parallel relative to the second rod; and
   a processor configured to determine a position of the block using an image of respective portions of the plurality of elongated markers;
   wherein the first rod has a first end, a second end, and a length between the first and second ends, the first end is exposed outside the block, and a part of the length is located within the block; and
   wherein the processor is further configured to determine a phase of a physiological cycle based on the determined position of the block.

4. The system of claim 3, wherein the processor is further configured to sort a plurality of images based on the determined phase.

5. A system for determining a position of an object, comprising:
- a block having a base;
- a plurality of elongated markers secured to the block, wherein the plurality of elongated markers comprises a first rod and a second rod, the first rod being non-parallel relative to the second rod; and
- an imaging system for obtaining an image of respective portions of the plurality of elongated markers;
- wherein the image includes an image of internal tissue of a patient.

6. The system of claim 5, further comprising a processor configured to determine a position of the block using the image.

7. The system of claim 5, wherein an end of the first rod is exposed outside the block.

8. The system of claim 5, wherein the block has a plurality of slots with a quantity that is greater than a quantity of the elongated markers, and wherein each of the slots is sized to accommodate at least one of the elongated markers.

9. The system of claim 5, wherein the plurality of elongated markers comprises a third rod that is non-parallel relative to the first and second rods, and the third rod and the second rod are partially within the block.

10. A system for determining a position of an object, comprising:
- a processor configured to obtain an image of portions of respective elongated members, and determine a position of an object that is coupled to the plurality of elongated members;
- wherein the elongated members are coupled to a block, and wherein the elongated members comprise a first marker and a second marker that is non-parallel relative to the first marker, and wherein the first marker has a first end, a second end, and a length between the first and second ends, the first end is exposed outside the block, and a part of the length is located within the block.

11. The system of claim 10, further comprising an imaging system for obtaining the image.

12. The system of claim 11, wherein the imaging system comprises a computed tomography system.

13. The system of claim 10, further comprising the plurality of elongated members.

14. The system of claim 10, wherein the object comprises a block to which the plurality of elongated members are secured.

15. The system of claim 10, wherein the object comprises a portion of a patient.

16. The system of claim 10, wherein the processor is configured to determine the position of the object by:
- determining positions of the portions of the plurality of elongated members in the image;
- determining relative orientation between the plurality of elongated members; and
- calculating the position of the object based on the determined positions of the portions and the determined relative orientation.

17. The system of claim 10, wherein the processor is further configured to determine a phase of a physiological cycle based on the determined position.

18. The system of claim 17, wherein the processor is further configured to sort a plurality of images based on the determined phase.

19. The system of claim 18, wherein the plurality of images comprises computed tomography images that are generated at different phases of a physiological cycle.

20. The system of claim 17, wherein the processor is further configured to determine a three dimensional image of the object that is associated with the determined phase.

21. The system of claim 10, wherein the second end of the first marker is exposed outside the block.

22. The system of claim 10, wherein the object has a plurality of slots with a quantity that is greater than a quantity of the elongated members, and wherein each of the slots is sized to accommodate at least one of the elongated members.

23. The system of claim 10, wherein the part of the length comprises a majority of the length.

24. The system of claim 10, wherein the elongated members comprise a third marker that is nonparallel relative to the first and second markers, wherein the third marker and the second marker are partially within the block.

25. A method of determining a position of an object, comprising:
- obtaining a first image of portions of respective elongated members; and
- determining a first position of an object using the first image;
- wherein the elongated members are couple to a block, and wherein the elongated members comprise a first marker and a second marker that is non-parallel relative to the first marker, and wherein the first marker has a first end, a second end, and a length between the first and second ends, the first end is exposed outside the block, and a part of the length is located within the block.

26. The method of claim 25, further comprising determining a first phase of a physiological cycle based on the determined position.

27. The method of claim 25, further comprising:
- obtaining a second image of portions of the respective elongated members; and
- determining a second position of the object using the second image.

28. The method of claim 27, further comprising using the first and the second images to form a three dimensional image of the object.

29. The method of claim 27, wherein the first image is associated with a first phase, and the second image is associated with a second phase that is different from the first phase.

30. The method of claim 29, further comprising:
- determining a first three dimensional image of the object using the first image;
- associating the first three dimensional image with the first phase;
- determining a second three dimensional image of the object using the second image; and
- associating the second three dimensional image with objective second phase.

31. The method of claim 30, further comprising displaying the first and the second three dimensional images in a sequence to form a video.

32. The method of claim 27, wherein the portions of the elongated members in the second image are different from the portions of the elongated members in the first image.

33. The method of claim 27, wherein the portions of the elongated members in the second image are the same as the portions of the elongated members in the first image.

34. The method of claim 25, wherein the first image is obtained using a computed tomography system.

35. The method of claim 25, wherein the object comprises a block, and the plurality of elongated members are secured to the block.

36. The method of claim 25, wherein the object comprises a portion of a patient.

37. The method of claim 25, wherein the first position of the object is determined by:
   determining positions of the portions of the plurality of elongated members in the first image;
   determining relative orientation between the plurality of elongated members; and
   calculating the first position of the object based on the determined positions of the portions and the determined relative orientation.

38. The method of claim 25, wherein the second end of the first marker is exposed outside the block.

39. The method of claim 25, wherein the object has a plurality of slots with a quantity that is greater than a quantity of the elongated members, and wherein each of the slots is sized to accommodate at least one of the elongated members.

40. The method of claim 25, wherein the part of the length comprises a majority of the length.

41. The method of claim 25, wherein the elongated members comprise a third marker that is non-parallel relative to the first and second markers, and the third marker and the second marker are partially within the block.

* * * * *